United States Patent
Hosoi et al.

(10) Patent No.: US 9,714,217 B2
(45) Date of Patent: Jul. 25, 2017

(54) SULFONIC ACID DERIVATIVE AND PHOTOACID GENERATOR

(75) Inventors: Yasuhiro Hosoi, Chiba (JP); Yuzuru Kaneko, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 227 days.

(21) Appl. No.: 13/574,683

(22) PCT Filed: Jan. 13, 2011

(86) PCT No.: PCT/JP2011/050454
§ 371 (c)(1),
(2), (4) Date: Jul. 23, 2012

(87) PCT Pub. No.: WO2011/093139
PCT Pub. Date: Aug. 4, 2011

(65) Prior Publication Data
US 2012/0289738 A1    Nov. 15, 2012

(30) Foreign Application Priority Data

Jan. 28, 2010 (JP) ................................. 2010-017483

(51) Int. Cl.
C07C 309/12 (2006.01)
C07C 381/12 (2006.01)
G03F 7/004 (2006.01)
C07C 25/18 (2006.01)
G03F 7/039 (2006.01)

(52) U.S. Cl.
CPC ............ *C07C 309/12* (2013.01); *C07C 25/18* (2013.01); *C07C 381/12* (2013.01); *G03F 7/0045* (2013.01); *C07C 2101/14* (2013.01); *G03F 7/0046* (2013.01); *G03F 7/0397* (2013.01)

(58) Field of Classification Search
None
See application file for complete search history.

(56) References Cited

U.S. PATENT DOCUMENTS 7,569,324 B2 *   8/2009   Kobayashi et al. ....... 430/270.1
2008/0124656 A1   5/2008   Kobayashi et al.
2010/0248143 A1   9/2010   Ito et al.

FOREIGN PATENT DOCUMENTS

| JP | 10-007650 | 1/1998 |
| JP | 2003-327572 | 11/2003 |
| JP | 2008-007410 | 1/2008 |
| JP | 2010-256856 | 11/2010 |

OTHER PUBLICATIONS

International Search Report, PCT/JP2011/050454, Feb. 22, 2011.
Mingxing Wang et al., New Anionic Photoacid Generator Bound Polymer Resists for EUV Lithography, Macromolecules, 2007, 40, 8220-8224, p. 8221, fig. 2, MTFB PAG.
Mingxing Wang et al., Fluorine-contained photoacid generators (PAGs) and corresponding polymer resists, Journal of Fluorine Chemistry, 2008, 129, 607-612, p. 608, fig. 1, MTFBS-TPS and VBzTFBS-TPS.

* cited by examiner

*Primary Examiner* — Clinton Brooks
(74) *Attorney, Agent, or Firm* — Young & Thompson

(57) ABSTRACT

Sulfonic acid derivatives of general formula $RCOOCH_2CH_2CFHCF_2SO_3\text{-}M^+$ are provided, wherein R represents a substituted or unsubstituted $C_{1-30}$ linear, branched, or cyclic hydrocarbon group, or a substituted or unsubstituted $C_{6-30}$ aryl group, and $M^+$ represents a counter cation. Photoacid generators and photoresists containing such sulfonic acid derivatives are also provided.

13 Claims, No Drawings

SULFONIC ACID DERIVATIVE AND PHOTOACID GENERATOR

TECHNICAL FIELD

This invention relates to a sulfonic acid derivative useful as a photoacid generator which, when irradiated with active radiation such as deep UV, KrF excimer laser light, ArF excimer laser light, $F_2$ excimer laser light, electron rays, X-rays or EUV (extreme ultraviolet radiation), easily decomposes to generate an acid, particularly useful as a photoacid generator for a chemical amplification type or chemically amplified photoresist material.

BACKGROUND ART

With semiconductor devices, for example, large-scale integrated circuit devices typified by DRAM, etc., there is an eager demand for even greater density, more integration or higher speed. In accordance with these trends, demands for the establishment of half-micron microfabrication technologies, for example, the development of photolithography technologies for the formation of fine patterns, have become increasingly intense in the field of production of various electronic devices. To form fine patterns by the photolithography technologies, it is necessary to increase resolution. The resolution (R) of a reduced projection exposure system is represented by Rayleigh's equation $R=k \cdot \lambda/NA$ (where $\lambda$ represents the wavelength of exposure light, NA represents the numerical aperture of a lens, and k represents the process factor. By shortening the wavelength $\lambda$ of active radiation (exposure light), which is used in forming a resist pattern, therefore, the resolution can be increased.

As photoresists suitable for short wavelengths, those of the chemical amplification type are proposed. The chemically amplified photoresists are characterized in that a proton acid is generated from a photoacid generator, which is a component contained therein, by irradiation with exposure light, and this proton acid causes an acid catalyst reaction with a resist resin or the like upon heating after exposure. Most of the photoresists which have been developed currently are of the chemical amplification type.

As acids generated upon exposure from photoacid generators, alkanesulfonic acids or partially or completely fluorinated alkanesulfonic acids are used.

The alkanesulfonic acid-generating photoacid generator generates an acid whose strength is weak. Thus, a protective group which facilitates deprotection is introduced into the resin for use in the chemically amplified resist, and scaling-down of designs is considered. To use the protective group whose deprotection is easy, a sulfonic acid having a large molecular size and low diffusibility, such as camphorsulfonic acid, has been used as an effective sulfonic acid. However, the use of the sulfonic acid with low diffusibility requires a large amount of the acid generated and, as a result, poses the problems that the amount of exposure is large and the productivity decreases.

Acid generators which generate completely fluorinated alkanesulfonic acids have sufficient acid strength against a deprotection reaction for a protective group whose deprotection is difficult, and most of these acid generators are in practical use. However, too high an acid strength thereof causes an unexpected reaction in the elimination reaction of the protective group for reversing the dissolution contrast of the resin, thereby arousing the problem that foreign matter occurs after alkali development or during resist stripping. Patent Document 1 reports that the problem of presenting foreign matter has been solved by using a publicly known sulfonic acid having moderate acid strength in which the alkyl group of the alkanesulfonic acid has been partially replaced by a fluorine atom, a nitro group or the like being an electron attractive group. With a compound which generates a sulfonic acid having 3 or more fluorine atoms, however, foreign matter occurs after alkali development or during resist stripping, leading to unsatisfactory results. Patent Document 2 reports that moderate acid strength is imparted, without occurrence of foreign matter, by using a compound generating a sulfonic acid in which an alkyl group and a perfluoroalkyl group have been introduced into the alpha-carbon atom of methanesulfonic acid. However, sufficient acid strength has not been obtained. Patent Document 3 discloses a sulfonic acid having high acid strength, but sufficient properties have not been obtained in connection with the occurrence of foreign matter.

PRIOR ART DOCUMENTS

Patent Documents

[Patent Document 1] JP-A-10-7650
[Patent Document 2] JP-A-2003-327572
[Patent Document 3] JP-A-2008-7410

SUMMARY OF THE INVENTION

Problems to be Solved by the Invention

The present invention has been accomplished in the light of the above-mentioned circumstances. It is an object of the present invention to provide a photoacid generator which does not produce foreign matter, which generates an acid having sufficient acid strength, and which is used for a resist material; and a sulfonic acid derivative suitable as an optically generated acid.

Means for Solving the Problems

An aspect of the present invention for solving the above-mentioned problems lies in a sulfonic acid derivative which is characterized by being represented by the following general formula (1):

[Chemical Formula 1]

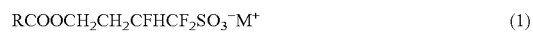

$$RCOOCH_2CH_2CFHCF_2SO_3^-M^+ \quad (1)$$

where R represents a substituted or unsubstituted $C_{1-30}$ linear, branched, or cyclic hydrocarbon group, or a substituted or unsubstituted $C_{6-30}$ aryl group, and $M^+$ represents a counter cation.

A second aspect of the present invention lies in the sulfonic acid derivative according to the first aspect, characterized in that the $M^+$ is a hydrogen ion, a metal ion, or an onium ion.

A third aspect of the present invention lies in a photoacid generator comprising the sulfonic acid derivative according to the first or second aspect.

Effects of the Invention

The sulfonic acid derivative of the present invention is a compound having a specific structure in which all of the α-positions and some of the β-positions have been substituted by fluorine, as indicated by the above general formula (1). This compound is useful as an acid generator which generates an acid having sufficient acid strength. When used as a photoresist, this compound has the effect of scarcely producing foreign matter after alkali development or at the time of stripping the resist.

MODE FOR CARRYING OUT THE INVENTION

Hereinbelow, the present invention will be described in detail.

The sulfonic acid derivative of the present invention is represented by the above general formula (1). The sulfonic acid derivative refers to a sulfonic acid and its salt. The sulfonic acid derivative of the present invention represented by the general formula (1) may be optically active or inactive.

Concrete examples of the unsubstituted $C_{1-30}$, preferably $C_{1-10}$, linear, branched, or cyclic monovalent hydrocarbon group, as R in the general formula (1), are a methyl group, an ethyl group, an n-propyl group, an i-propyl group, an n-butyl group, a t-butyl group, an n-pentyl group, an i-pentyl group, an n-hexyl group, an i-hexyl group, an n-octyl group, an i-octyl group, a 2-ethylhexyl group, an n-dodecyl group, a cyclopropyl group, a cyclopentyl group, a cyclohexyl group, a group having a norbornene skeleton, a group having a tricyclododecane skeleton, and a group having a tetracyclododecane skeleton or an adamantane skeleton.

Examples of the substituent for the above hydrocarbon group are an aryl group, an alkenyl group, and an organic group containing a hetero-atom such as a halogen atom, an oxygen atom, a nitrogen atom, a sulfur atom, a phosphorus atom, or a silicon atom.

Concrete examples of the $C_{1-30}$, preferably $C_{1-10}$, linear, branched, or cyclic monovalent hydrocarbon group substituted by the substituent are a benzyl group, a methoxymethyl group, a methylthiomethyl group, an ethoxymethyl group, a phenoxymethyl group, a methoxycarbonylmethyl group, an ethoxycarbonylmethyl group, an acetylmethyl group, a fluoromethyl group, a trifluoromethyl group, a chloromethyl group, a trichloromethyl group, a 2-fluoropropyl group, a trifluoroacetylmethyl group, a trichloroacetylmethyl group, a pentafluorobenzoylmethyl group, an aminomethyl group, a cyclohexylaminomethyl group, a diphenylphosphinomethyl group, a trimethylsilylmethyl group, a 2-phenylethyl group, a 3-phenylpropyl group, and a 2-aminoethyl group.

Concrete examples of the unsubstituted $C_{6-30}$ preferably $C_{6-10}$ aryl group are a phenyl group, a 1-naphthyl group, a 2-naphthyl group, a 1-anthryl group, and a 1-phenanthryl group.

Examples of the substituent for the above aryl group are an alkyl group, and an organic group containing a heteroatom such as a halogen atom, an oxygen atom, a nitrogen atom, a sulfur atom, a phosphorus atom, or a silicon atom.

Concrete examples of the $C_{6-30}$ aryl group substituted by the substituent are an o-tolyl group, a m-tolyl group, a p-tolyl group, a p-t-butylphenyl group, a p-methoxyphenyl group, a mesityl group, an o-cumenyl group, a 2,3-xylyl group, a p-fluorophenyl group, a p-trifluoromethylphenyl group, a p-bromophenyl group, a p-chlorophenyl group, and a p-iodophenyl group.

As the cation $M^+$ which forms a salt with the sulfonic acid, a hydrogen ion, a metal ion, and an onium ion can be named concretely.

As a more concrete metal ion, there can be named monovalent cations from Group 1 elements, such as a lithium ion, a sodium ion and a potassium ion; divalent cations from Group 2 elements, such as a magnesium ion (II) and a calcium ion (II); transition metal ions such as an iron ion (II), an iron ion (III), a copper ion (I), a copper ion (II), a nickel ion (II) and a nickel ion (III); and heavy metal ions such as a lead ion. Any of these metal ions may have formed a complex with a ligand.

As the onium ion, onium salts constituted by a nitrogen atom, a sulfur atom, a halogen atom, a phosphorus atom, etc. are named. Their concrete examples are onium salts constituted by a nitrogen atom, such as an ammonium ion, a methylammonium ion, a dimethylammonium ion, a trimethylammonium ion, a tetramethylammonium ion, a phenylammonium ion, a diphenylammonium ion, a triphenylammonium ion, a dimethylphenylammonium ion, a trimethylphenylammonium ion, a pyridinium ion, an alkylpyridinium ion, a fluoropyridinium ion, a chloropyridinium ion, a bromopyridinium ion, a tetramethylammonium ion, an imidazolium ion, and a quinolinium ion; onium salts constituted by a sulfur atom, such as a trimethylsulfonium ion, a tributylsulfonium ion, a dimethyl(2-oxocyclohexyl)sulfonium ion, a bis(2-oxocyclohexyl)methylsulfonium ion, a (10-camphenoyl)methyl(2-oxocyclohexyl)sulfonium ion, a (2-norbornyl)methyl(2-oxocyclohexyl)sulfonium ion, a triphenylsulfonium ion, a diphenyltolylsulfonium ion, a diphenylxylylsulfonium ion, a mesityldiphenylsulfonium ion, a (t-butylphenyl)diphenylsulfonium ion, an (octylphenyl)diphenylsulfonium ion, a (cyclohexylphenyl)diphenylsulfonium ion, a biphenyldiphenylsulfonium ion, a (hydroxymethylphenyl)diphenylsulfonium ion, a (methoxymethylphenyl)diphenylsulfonium ion, an (acetylphenyl)diphenylsulfonium ion, a (benzoylphenyl)diphenylsulfonium ion, a (hydroxycarbonylphenyl)diphenylsulfonium ion, a (methoxycarbonylphenyl)diphenylsulfonium ion, a (trifluoromethylphenyl)diphenylsulfonium ion, a (fluorophenyl)diphenylsulfonium ion, a (chlorophenyl)diphenylsulfonium ion, a (bromophenyl)diphenylsulfonium ion, an (iodophenyl)diphenylsulfonium ion, a pentafluorophenyldiphenylsulfonium ion, a (hydroxyphenyl)diphenylsulfonium ion, a (methoxyphenyl)diphenylsulfonium ion, a (butoxyphenyl)diphenylsulfonium ion, an (acetyloxyphenyl)diphenylsulfonium ion, a (benzoyloxyphenyl)diphenylsulfonium ion, a (dimethylcarbamoylphenyl)diphenylsulfonium ion, an (acetylamidophenyl)diphenylsulfonium ion, a phenylditolylsulfonium ion, a phenyldixylylsulfonium ion, a dimesitylphenylsulfonium ion, a bis(t-butylphenyl)phenylsulfonium ion, a bis(octylphenyl)phenylsulfonium ion, a bis(cyclohexylphenyl)phenylsulfonium ion, a dibiphenylphenylsulfonium ion, a bis(hydroxymethylphenyl)phenylsulfonium ion, a bis(methoxymethylphenyl)phenylsulfonium ion, a bis(acetylphenyl)phenylsulfonium ion, a bis(benzoylphenyl)phenylsulfonium ion, a bis(hydroxycaronylphenyl)phenylsulfonium ion, a bis(methoxycarbonylphenyl)phenylsulfonium ion, a bis(trifluoromethylphenyl)phenylsulfonium ion, a bis(fluorophenyl)phenylsulfonium ion, a bis(chlorophenyl)phenylsulfonium ion, a bis(bromophenyl)phenylsulfonium ion, a bis(iodophenyl)phenylsulfonium ion, a dipentafluorophenylphenylsulfonium ion, a bis(hydroxyphenyl)phenylsulfonium ion, a bis(methoxyphenyl)phenylsulfonium ion, a bis(butoxyphenyl)phenylsulfonium ion, a bis(acetyloxyphenyl)phenylsulfonium ion, a bis(benzoyloxyphenyl)phenylsulfonium ion, a bis(dimethylcarbamoylphenyl)phenylsulfonium ion, a bis(acetylamidophenyl)phenylsulfoniumion, a tristolylsulfonium ion, a trisxylylsulfonium ion, a trismesitylphenylsulfonium ion, a tris(t-butylphenyl)sulfoniumion, a tris(octylphenyl)sulfonium ion, a tris(cyclohexylphenyl)sulfonium ion, a tribiphenylsulfonium ion, a tris(hydroxymethylphenyl)sulfonium ion, a tris(methoxymethylphenyl)sulfonium ion, a tris(acetylphenyl)sulfoniumion, a tris(benzoylphenyl)sulfonium ion, a tris (hydroxycarbonylphenyl)sulfonium ion, a tris (methoxycarbonylphenyl)sulfonium ion, a tris (trifluoromethylphenyl)sulfonium ion, a tris(fluorophenyl) sulfonium ion, a tris(chlorophenyl)sulfonium ion, a tris (bromophenyl)sulfonium ion, a tris(iodophenyl)sulfonium ion, a dipentafluorophenylsulfonium ion, a tris(hydroxyphenyl)sulfonium ion, a tris(methoxyphenyl)sulfoniumion, a tris(butoxyphenyl)sulfonium ion, a tris(acetyloxyphenyl)sulfonium ion, a tris(benzoyloxyphenyl)sulfonium ion, a tris(dimethylcarbamoylphenyl)sulfonium ion, a tris(acetylamidophenyl)sulfoniumion, a methyldiphenylsulfonium ion, an ethyldiphenylsulfoniumion, a butyldiphenylsulfoniumion, a hexyldiphenylsulfonium ion, an octyldiphenylsulfonium ion, a cyclohexyldiphenylsulfonium ion, a 2-oxocyclohexyldiphenylsulfonium ion, a norbornyldiphenylsulfonium ion, a camphenoyldiphenylsulfonium ion, a pinanoyldiphenylsulfonium ion, a naphthyldiphenylsulfoniumion, ananthranyldiphenylsulfoniumion, a benzyldiphenylsulfonium ion, a trifluoromethyldiphenylsulfonium ion, a methoxycarbonylmethyldiphenylsulfonium ion, a butoxycarbonylmethyldiphenylsulfonium ion, a benzoylmethyldiphenylsulfonium ion, a (methylthiophenyl)diphenylsulfonium ion, a (phenylthiophenyl)diphenylsulfonium ion, an (acetylphenylthiophenyl)diphenylsulfonium ion, a dimethylphenylsulfonium ion, a diethylphenylsulfonium ion, a dibutylphenylsulfonium ion, a dihexylphenylsulfonium ion, a dioctylphenylsulfonium ion, a dicyclohexylphenylsulfonium ion, a bis(2-oxocyclohexyl) phenylsulfonium ion, a dinorbornylphenylsulfonium ion, a dicamphenoylphenylsulfonium ion, a dipinanoylphenylsulfonium ion, a dinaphthylphenylsulfonium ion, a dibenzylphenylsulfonium ion, a trifluoromethyldiphenylsulfonium ion, a bis(methoxycarbonylmethyl)phenylsulfonium ion, a bis(butoxycarbonylmethyl)phenylsulfonium ion, a dibenzoylmethylphenylsulfonium ion, a bis(methylthiophenyl)phenylsulfonium ion, a bis(phenylthiophenyl)phenylsulfonium ion, a bis(acetylphenylthiophenyl)phenylsulfonium ion, a dimethyl(2-oxocyclohexyl)sulfonium ion, a bis(2-oxocyclohexyl)methylsulfonium ion, a (10-camphenoyl)methyl(2-oxocyclohexyl)sulfonium ion, a (2-norbornyl)methyl(2-oxocyclohexyl)sulfonium ion, a trimethylsulfonium ion, a triethylsulfonium ion, a tributylsulfonium ion, a dihexylmethylsulfonium ion, a trioctylsulfonium ion, a dicyclohexylethylsulfonium ion, a methyltetrahydrothiophenium ion, a methyltetrahydrothiophenium ion, a triphenyloxosulfoniium ion, and a bis[4-(diphenylsulfonio)phenyl]sulfide-bision; and onium salts constituted by a phosphorus atom, such as a tetraphenylphosphonium ion. Examples of the halonium salts are a diphenyliodonium ion, a bis-(t-butylphenyl)iodonium cation, a (methoxyphenyl)phenyliodonium ion, a (butoxyphenyl)phenyliodonium ion, a trifluoroethylphenyliodonium ion, and a pentafluorophenylphenyliodonium ion. The preferred examples are the sulfonium ions and the iodonium ions.

The sulfonic acid derivative represented by the general formula (1) is a compound having a specific structure in which all of the α-positions and some of the β-positions have been substituted by fluorine. Thus, it is useful as an acid generator which efficiently decomposes upon irradiation with active radiation, such as KrF excimer laser light, ArF excimer laser light, $F_2$ excimer laser light, electron rays, X-rays, or EUV, to generate an acid having sufficient acid strength. When it is used for a photosensitive resin composition (photoresist), moreover, no side reaction occurs. Hence, foreign matter does not occur after alkali development or at the time of resist stripping.

The sulfonic acid derivative of Patent Document 3 is a compound having four fluorine atoms as a result of fluorine substitution at all of the α-positions and the β-positions. Probably because of too high an acid strength thereof, therefore, foreign matter occurs after alkali development or at the time of resist stripping. Patent Document 3 has no idea about the sulfonic acid derivative represented by the general formula (1) of the present invention in which all of the α-positions and some of the β-positions have been substituted by fluorine. Even if the manufacturing method described in Patent Document 3 is based, and the raw material, for example, is changed, moreover, the sulfonic acid derivative of the present invention cannot be produced. A sulfonic acid derivative having two fluorine atoms at the α-positions, on the other hand, is insufficient in acid strength.

Generally, a sulfonic acid derivative having 3 fluorine atoms involves the problem that foreign matter occurs after alkali development or during resist stripping. The sulfonic acid derivative of a specific structure represented by the general formula (1) according to the present invention, by contrast, can impart sufficient acid strength and can be free from the occurrence of foreign matter.

The sulfonic acid derivative of the present invention can be used as a photoacid generator of an ordinary photosensitive resin composition, concretely, a two-component positive photosensitive resin composition comprising a photoacid generator and a resin having a group which decomposes when reacted with an acid to become alkali-soluble; a three-component positive photosensitive resin composition comprising an alkali-soluble resin, a photoacid generator, and a dissolution-inhibiting compound which has an acid-decomposable group and possesses insolubilizing power on the alkali-soluble resin; or a negative photosensitive resin composition comprising an alkali-soluble resin and a crosslinking agent having the action of crosslinking the alkali-soluble resin with an acid.

The sulfonic acid derivative of the general formula (1) according to the present invention can be synthesized, for example, along the following reaction path: First, 4-bromo-1,1,2-trifluoro-1-butene is acetylated with sodium acetate, followed by hydrolysis with a base or the like. Further, sulfonation using a hydrogensulfite gives a sulfonate. This salt is subjected to salt exchange with the aforementioned $M^+$ based on the customary method. Then, the resulting salt is esterified, for example, with an acid anhydride or an acid halide, whereby a sulfonic acid represented by the general formula (1) can be obtained.

[Chemical formula 2]

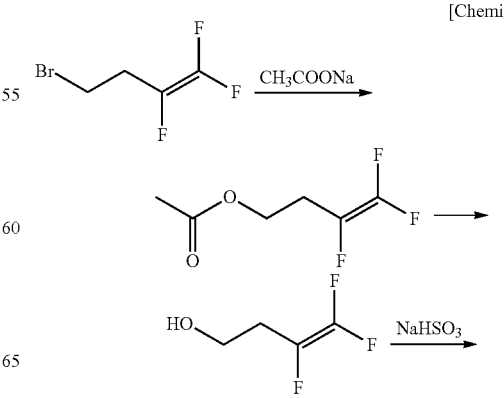

-continued

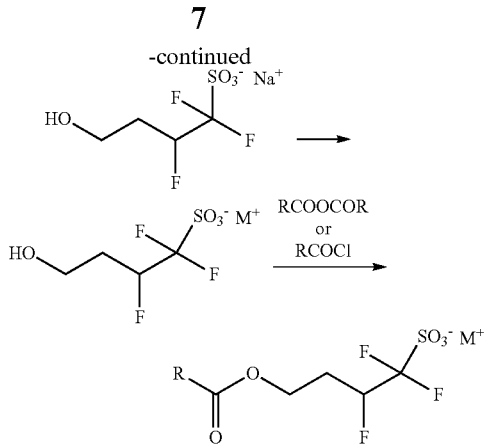

EXAMPLES

The present invention will be described below based on its working examples, but this invention is in no way limited by these examples.

Example 1

Example 1-1

Synthesis of sodium 1,1,2-trifluoro-4-hydroxybutanesulfonate

[Chemical formula 3]

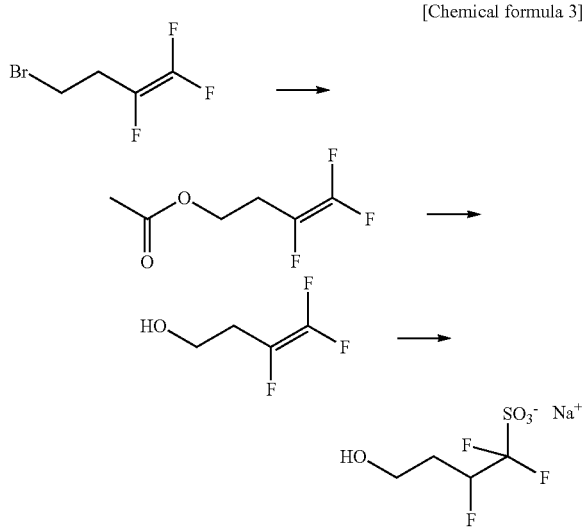

<First Step>

4-Bromo-1,1,2-trifluoro-1-butene (36.9 g) and 65.4 g of sodium acetate were dissolved in 156.5 g of acetic acid, and the solution was heated to 115° C. Then, the system was stirred for 40 hours, and the reaction mixture was cooled to 90° C., followed by adding 626 g of distilled water. Then, the mixture was cooled to room temperature, and extracted twice using 128 g of t-butyl methyl ether. Then, the extract was washed with 165 g of an aqueous solution of sodium carbonate to remove the remaining acid. Then, the solvent was distilled off using a rotary evaporator to obtain 4-acetoxy-1,1,2-trifluoro-1-butene. In the crude state, this substance amounted to 25.6 g. The results of its $^1$H NMR measurement are shown below.

$^1$H NMR (400 MHz, CDCl$_3$) δ2.07 (s, 3H), 2.63 (d, t, d, d, 2H), 4.24 (t, 2H)

<Second Step>

The 4-acetoxy-1,1,2-trifluoro-1-butene (25.0 g) and 40.3 g of potassium carbonate were dissolved in 49 g of methanol and 49 g of distilled water. The solution was stirred for 15 hours at room temperature, and filtered to remove solids precipitated by the reaction. Then, the desired material was extracted with dichloromethane. Then, the extract was distilled for purification to obtain 13.8 g of 3,4,4-trifluoro-3-buten-1-ol. The results of the $^1$H NMR measurement of this substance are shown below.

$^1$H NMR (400 MHz, CDCl$_3$) δ2.2 (s, 1H), 2.55 (d, t, d, d, 2H), 3.83 (t, 2H)

<Third Step>

The 3,4,4-trifluoro-3-buten-1-ol (11.9 g), 29.5 g of sodium hydrogensulfite, and 14.3 g of sodium sulfite were dissolved in 214 g of distilled water, followed by heating the solution to 90° C. The system was stirred for 15 hours, and the reaction mixture was cooled to 25° C. or lower. Then, the aqueous layer was washed with 24 g of toluene. Then, the solvent was distilled off by a rotary evaporator to obtain 18.46 g of sodium 1,1,2-trifluoro-4-hydroxybutanesulfonate. This substance was confirmed to be the desired product based on the results of $^1$H NMR and ion chromatography measurements. The results of its $^1$H NMR measurement are shown below.

$^1$H NMR (400 MHz, CDCl$_3$) δ1.9-2.4 (m, 2H), 3.5-3.7 (m, 2H), 4.9-5.2 (m, 1H)

Example 1-2

Synthesis of triphenylsulfonium 4-(cyclohexylcarbonyloxy)-1,1,2-trifluorobutanesulfonate

[Chemical formula 4]

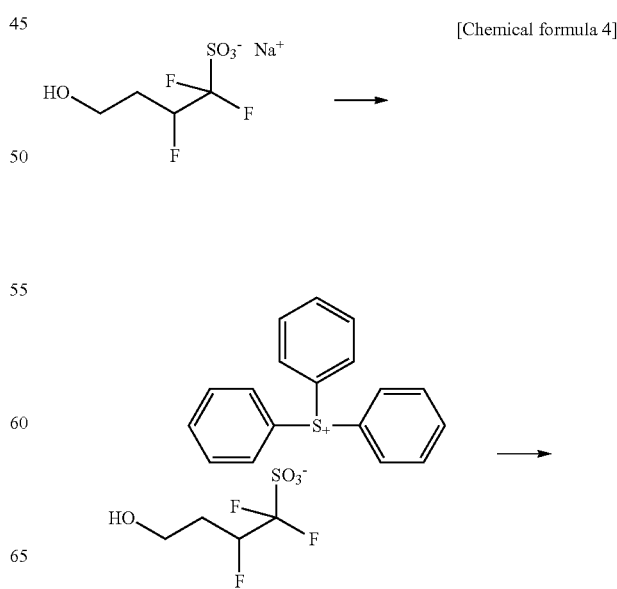

-continued

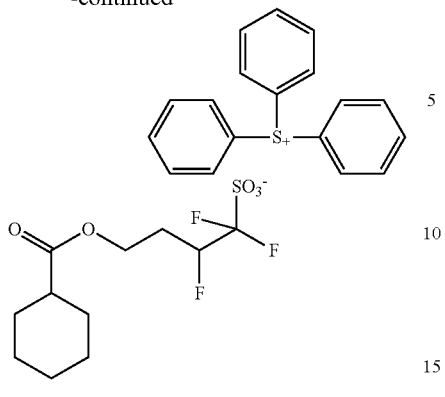

Example 2

Synthesis of tris(p-t-butylphenyl)sulfonium 4-(cyclohexylcarbonyloxy)-1,1,2-trifluorobutanesulfonate

[Chemical formula 5]

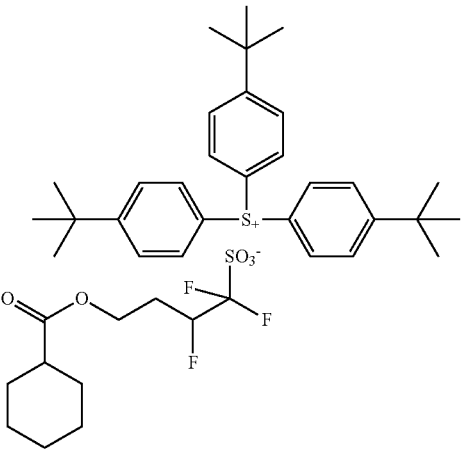

<First Step>

The sodium 1,1,2-trifluoro-4-hydroxybutanesulfonate (17.6 g) and 34.4 g of triphenylsulfonium methanesulfonate were added to 106 g of water and 360 g of dichloromethane, and the mixture was stirred for 3 hours. After liquid-liquid separation, the organic layer was subjected to a rotary evaporator, where the solvent was distilled off to obtain 32.4 g of triphenylsulfonium 1,1,2-trifluoro-4-hydroxybutanesulfonate. The results of the $^1$H NMR measurement of this substance are shown below.

$^1$H NMR (400 MHz, CDCl$_3$) δ1.9-2.4 (m, 2H), 3.5-3.7 (m, 2H), 4.9-5.2 (m, 1H), 7.66-7.80 (m, 15H)

<Second Step>

The triphenylsulfonium 1,1,2-trifluoro-4-hydroxybutanesulfonate (27.4 g), 7.07 g of triethylamine, and 0.7 g of N,N,N',N'-tetramethylethylenediamine were dissolved in 137 g of dichloromethane. Then, 10.2 g of cyclohexanecarbonyl chloride was added at 15° C. or lower, and the mixture was heated to 20° C. The system was stirred for 3 hours, and the reaction mixture was cooled to 15° C. or lower. An 8% aqueous solution of sodium hydrogen carbonate was added to terminate the reaction. Then, 68 g of dichloromethane was added, and the mixture was stirred to extract the desired compound into the dichloromethane layer. Then, the organic layer was repeatedly washed with distilled water until the pH of the separated aqueous layer became 7. Then, the solvent was distilled off by a rotary evaporator to obtain 23.7 g of triphenylsulfonium 4-(cyclohexylcarbonyloxy)-1,1,2-trifluorobutanesulfonate. This substance was confirmed to be the desired product based on the results of $^1$H NMR and ion chromatography measurements. The results of its $^1$H NMR measurement are shown below.

$^1$H NMR (400 MHz, DMSO-d$^6$) δ1.1-1.8 (m, 10H), 1.9-2.3 (m, 3H), 4.0-4.2 (m, 2H), 4.8-5.1 (m, 1H), 7.7-7.8 (m, 15H)

Synthesis was performed in the same manner as in <First step> of Example 1-2, except that 34.4 g of triphenylsulfonium methanesulfonate was replaced by 48.3 g of tris(p-t-butylphenyl)sulfonium methanesulfonate. As a result, 44.0 g of tris(p-t-butylphenyl)sulfonium 1,1,2-trifluoro-4-hydroxybutanesulfonate was obtained. Then, synthesis was performed in the same manner as in <Second step> of Example 1-2, except that 27.4 g of triphenylsulfonium 1,1,2-trifluoro-4-hydroxybutanesulfonate was replaced by 37.2 g of tris(p-t-butylphenyl)sulfonium 1,1,2-trifluoro-4-hydroxybutanesulfonate. As a result, 32.7 g of tris(p-t-butylphenyl)sulfonium 4-(cyclohexylcarbonyloxy)-1,1,2-trifluorobutanesulfonate was obtained. This substance was confirmed to be the desired product based on the results of $^1$H NMR and ion chromatography measurements. The results of its $^1$H NMR measurement are shown below.

$^1$H NMR (400 MHz, DMSO-d$^6$) δ1.1-1.7 (m, 37H), 1.9-2.3 (m, 3H), 4.0-4.2 (m, 2H), 4.8-5.1 (m, 1H), 7.6-7.8 (m, 12H)

Example 3

Synthesis of bis(p-t-butylphenyl)iodonium 4-(cyclohexylcarbonyloxy)-1,1,2-trifluorobutanesulfonate

[Chemical formula 6]

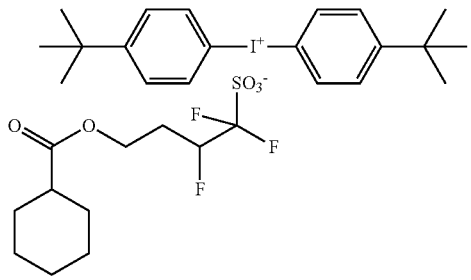

Synthesis was performed in the same manner as in <First step> of Example 1-2, except that 34.4 g of triphenylsulfonium methanesulfonate was replaced by 44.8 g of bis(4-t-butylphenyl)iodonium methanesulfonate. As a result, 41.3 g of bis(p-t-butylphenyl)iodonium 1,1,2-trifluoro-4-hydroxybutanesulfonate was obtained. Then, synthesis was performed in the same manner as in <Second step> of Example 1-2, except that 27.4 g of triphenylsulfonium 1,1,2-trifluoro-4-hydroxybutanesulfonate was replaced by 35.0 g of bis(p-t-butylphenyl)iodonium 1,1,2-trifluoro-4-hydroxybutanesulfonate. As a result, 28.2 g of bis(p-t-butylphenyl)iodonium 4-(cyclohexylcarbonyloxy)-1,1,2-trifluorobutanesulfonate was obtained. This substance was confirmed to be the desired product based on the results of $^1$H NMR and ion chromatography measurements. The results of its $^1$H NMR measurement are shown below.

$^1$H NMR (400 MHz, DMSO-d$^6$) δ1.1-1.7 (m, 28H), 1.9-2.3 (m, 3H), 4.0-4.2 (m, 2H), 4.8-5.1 (m, 1H), 7.3-8.0 (m, 8H)

Example 4

Synthesis of triphenylsulfonium 4-(p-t-butylbenzoyloxy)-1,1,2-trifluorobutanesulfonate

[Chemical formula 7]

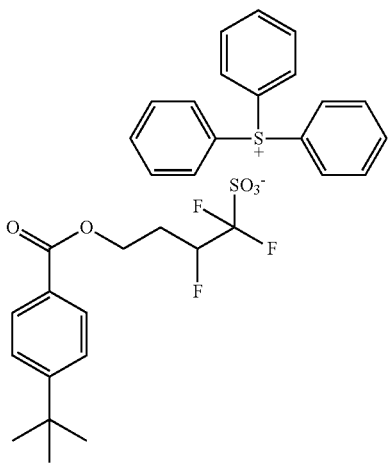

Synthesis was performed in the same manner as in Example 1-2, except that 10.2 g of cyclohexanecarbonyl chloride was replaced by 13.7 g of p-t-butylbenzoyl chloride. As a result, 28.3 g of triphenylsulfonium 4-(p-t-butylbenzoyloxy)-1,1,2-trifluorobutanesulfonate was obtained. This substance was confirmed to be the desired product based on the results of $^1$H NMR and ion chromatography measurements. The results of its $^1$H NMR measurement are shown below.

$^1$H NMR (400 MHz, DMSO-d$^6$) δ1.3 (s, 9H), 2.0-2.3 (m, 2H), 4.2-4.4 (m, 2H), 4.9-5.2 (m, 1H), 7.4-8.1 (m, 19H)

Example 5

Synthesis of triphenylsulfonium 4-pivaloyloxy-1,1,2-trifluorobutanesulfonate

[Chemical formula 8]

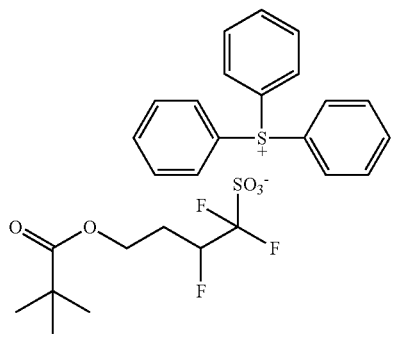

Synthesis was performed in the same manner as in Example 1-2, except that 10.2 g of cyclohexanecarbonyl chloride was replaced by 8.4 g of pivaloyl chloride. As a result, 25.8 g of triphenylsulfonium 4-pivaloyloxy-1,1,2-trifluorobutanesulfonate was obtained. This substance was confirmed to be the desired product based on the results of $^1$H NMR and ion chromatography measurements. The results of its $^1$H NMR measurement are shown below.

$^1$H NMR (400 MHz, DMSO-d$^6$) δ1.2 (s, 9H), 1.9-2.2 (m, 2H), 4.0-4.2 (m, 2H), 4.8-5.1 (m, 1H), 7.6-7.8 (m, 15H)

[Preparation and Characteristics Evaluation of Photoresist]

[Chemical formula 9]

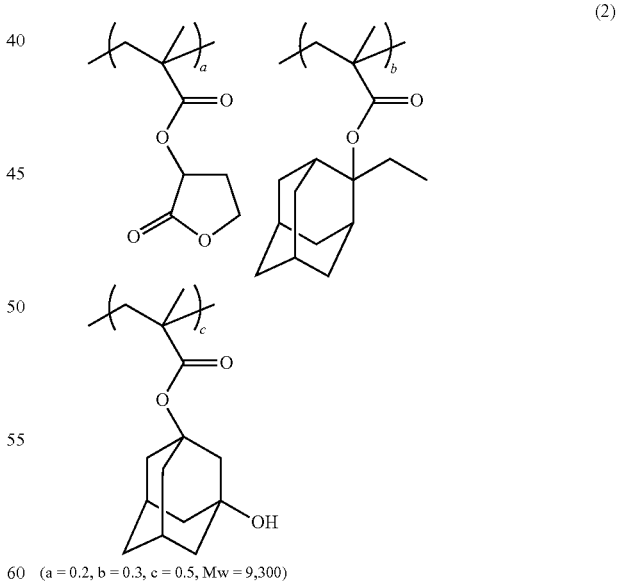

(a = 0.2, b = 0.3, c = 0.5, Mw = 9,300)

The triphenylsulfonium 4-(cyclohexylcarbonyloxy)-1,1,2-trifluorobutanesulfonate synthesized in Example 1 (2 parts by weight), 100 parts by weight of a polymer having the constitutional units indicated by the above general formula (2), and 0.2 part by weight of triethanolamine were dissolved in 525 parts by weight of propylene glycol monomethyl ether acetate. The solution was filtered through a PTFE filter to prepare a photosensitive resin composition solution. Then, the photosensitive resin composition solution was spin-coated on a silicon wafer, and then pre-baked on a hotplate for 90 seconds at 110° C. to obtain a resist film having a film thickness of 500 nm. This film was exposed by an ArF excimer laser stepper (wavelength 193 nm), and then post-baked for 90 seconds at 110° C. Then, the baked film was developed for 60 seconds with a 2.38% aqueous solution of tetramethylammonium hydroxide, and rinsed for 30 seconds with pure water.

As a result, a satisfactory pattern was obtained, and observations of the top of the pattern after exposure and the top of the silicon substrate after stripping showed no presence of foreign matter. The observations were made using a surface detect observation device produced by KLA-Tencor Corporation (model: KLA2351). An acid generated by exposure was confirmed to have sufficient acid strength.

For purposes of comparison, a resist was prepared using triphenylsulfonium trifluoromethanesulfonate instead of triphenylsulfonium 4-(cyclohexylcarbonyloxy)-1,1,2-trifluorobutanesulfonate, whereafter a resist film was obtained, exposed, post-baked, and developed. As a result, foreign matter was present in large amounts on the pattern after exposure and on the silicon substrate after stripping.

The invention claimed is:

1. A photoresist, comprising:
a photoacid generator of formula (1):

$RCOOCH_2CH_2CFHCF_2SO_3^- M^+$ (1)

wherein R is a linear, branched, or cyclic hydrocarbon group having from 4 to 30 carbon atoms, or an aryl group having from 6 to 30 carbon atoms,
the hydrocarbon group and the aryl group are substituted or unsubstituted, and
$M^+$ is a counter cation; and
a polymer.

2. The photoacid generator according to claim 1, wherein R is a cyclic hydrocarbon group having from 4 to 30 carbon atoms, or an aryl group having from 6 to 30 carbon atoms.

3. The photoacid generator according to claim 1, wherein M+ is a sulfonium ion or an iodonium ion.

4. The photoresist according to claim 1, wherein M+ is a counter cation selected from the group consisting of hydrogen ion, metal ion, and onium ion.

5. A photoresist, comprising
a sulfonic acid derivative of formula (1):

$RCOOCH_2CH_2CFHCF_2SO_3^- M^+$ (1)

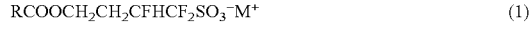

wherein R is a linear, branched or cyclic hydrocarbon group having from 4 to 30 carbon atoms, or an aryl group having from 6 to 30 carbon atoms, wherein the hydrocarbon group and the aryl group are substituted or unsubstituted, and $M^+$ is a counter cation; and
a polymer.

6. The photoresist according to claim 5, wherein the polymer has a protecting group.

7. The photoresist according to claim 5, wherein the sulfonic acid derivative is configured to function as a photoacid generator.

8. A method for manufacturing an electronic device, comprising performing a photolithography using the photoresist according to claim 5.

9. The photoresist according to claim 5, wherein the aryl group having from 6 to 30 carbon atoms is selected from the group consisting of a phenyl group, a 1-naphthyl group, a 2-naphthyl group, a 1-anthryl group, and a 1-phenanthryl group.

10. The photoresist according to claim 9, wherein the aryl group is substituted with at least one sustituent selected from the group consisting of an o-tolyl group, a m-tolyl group, a p-tolyl group, a p-t-butylphenyl group, a p-methoxyphenyl group, a mesityl group, an o-cumenyl group, a 2,3-xylyl group, a p-fluorophenyl group, a p-trifluoromethylphenyl group, a p-bromophenyl group, a p-chlorophenyl group, and a p-iodophenyl group.

11. A photoresist, comprising:
a photoacid generator comprising a sulfonic acid derivative, the derivative being $M^+$ 4-(cyclohexylcarbonyloxy)-1,1,2-trifluorobutanesulfonate, $M^+$ 4-(p-t-butylbenzoyloxy)-1,1,2-trifluorobutanesulfonate, or $M^+$ 4-pivaloyloxy-1,1,2-trifluorobutanesulfonate, wherein $M^+$ is an onium salt counter cation; and
a polymer resin,
wherein the photoacid generator is configured to decompose to generate an acid when irradiated with active radiation.

12. The photoresist according to claim 11, wherein the sulfonic acid derivative is selected from the group consisting of:
triphenylsulfonium 4-(cyclohexylcarbonyloxy)-1,1,2-trifluorobutanesulfonate,
tris(p-t-butylphenyl)sulfonium 4-(cyclohexylcarbonyloxy)-1,1,2-trifluorobutanesulfonate,
bis(p-t-butylphenyl)iodonium 4-(cyclohexylcarbonyloxy)-1,1,2-trifluorobutanesulfonate,
triphenylsulfonium 4-(p-t-butylbenzoyloxy)-1,1,2-trifluorobutanesulfonate, and
triphenylsulfonium 4-pivaloyloxy-1,1,2-trifluorobutanesulfonate.

13. The photoresist according to claim 11, wherein the polymer comprises the units represented by formula (2):

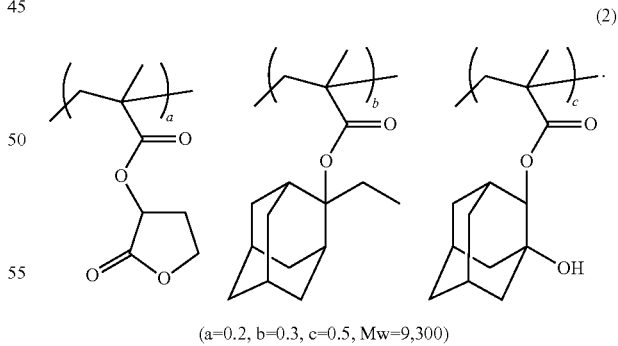

(a=0.2, b=0.3, c=0.5, Mw=9,300)